United States Patent
Huh et al.

(10) Patent No.: US 9,553,270 B2
(45) Date of Patent: Jan. 24, 2017

(54) MATERIAL FOR ORGANIC LIGHT-EMITTING DEVICE, AND ORGANIC LIGHT-EMITTING DEVICE USING SAME

(75) Inventors: Jungoh Huh, Seoul (KR); Tae Yoon Park, Daejeon (KR); Jungi Jang, Daejeon (KR); Sung Kil Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 390 days.

(21) Appl. No.: 14/240,855

(22) PCT Filed: Sep. 6, 2012

(86) PCT No.: PCT/KR2012/007183
§ 371 (c)(1),
(2), (4) Date: Feb. 25, 2014

(87) PCT Pub. No.: WO2013/036043
PCT Pub. Date: Mar. 14, 2013

(65) Prior Publication Data
US 2014/0197402 A1 Jul. 17, 2014

(30) Foreign Application Priority Data
Sep. 9, 2011 (KR) .................. 10-2011-0091943

(51) Int. Cl.
*H01L 51/00* (2006.01)
*H01L 51/50* (2006.01)
(Continued)

(52) U.S. Cl.
CPC ......... *H01L 51/0052* (2013.01); *C07D 307/91* (2013.01); *C09K 11/06* (2013.01);
(Continued)

(58) Field of Classification Search
CPC .. C07D 307/91; H01L 51/0052; H01L 51/006; H01L 51/0061; H01L 51/0073; H01L 51/0074; H01L 51/50; H01L 51/5012; H01L 51/5056; H01L 51/5064; H01L 51/5072; H01L 51/5088; C09K 11/06
See application file for complete search history.

(56) References Cited

U.S. PATENT DOCUMENTS

| | | | |
|---|---|---|---|
| 5,281,489 A * | 1/1994 | Mori .................... | C09K 11/06 313/498 |
| 8,129,038 B2 * | 3/2012 | Yabunouchi ......... | C07D 307/91 313/504 |

(Continued)

FOREIGN PATENT DOCUMENTS

| CN | 101432272 A | 5/2009 |
|---|---|---|
| CN | 102046613 A | 5/2011 |

(Continued)

OTHER PUBLICATIONS

Journal of Materials Chemistry, Royal Society of Chemistry, GB, vol. 15, No. 31, pp. 3233-3240, Date: 2005.

(Continued)

*Primary Examiner* — Dawn Garrett
(74) *Attorney, Agent, or Firm* — Dentons US LLP

(57) ABSTRACT

The present invention provides an organic light emitting device including a dibenzothiophene-based compound and an organic material layer composed of one more layers including a first electrode, a second electrode and a light emitting layer disposed between the first electrode and the second electrode, in which one or more layers of the organic material layer include the dibenzothiophene-based compound of Formula 1 or a compound in which a heat curable or photo curable functional group is introduced into the dibenzothiophene-based compound.

17 Claims, 1 Drawing Sheet

(51) Int. Cl.
*C09K 11/06* (2006.01)
*C07D 307/91* (2006.01)

(52) U.S. Cl.
CPC ........ *H01L 51/006* (2013.01); *H01L 51/0061* (2013.01); *H01L 51/0073* (2013.01); *H01L 51/0074* (2013.01); *H01L 51/50* (2013.01); *H01L 51/5012* (2013.01); *H01L 51/5056* (2013.01); *H01L 51/5064* (2013.01); *H01L 51/5072* (2013.01); *H01L 51/5088* (2013.01)

(56) References Cited

U.S. PATENT DOCUMENTS

| | | | |
|---|---|---|---|
| 2003/0044518 A1 | 3/2003 | Senoo et al. | |
| 2004/0124766 A1* | 7/2004 | Nakagawa | H01L 51/0064 313/504 |
| 2007/0224446 A1 | 9/2007 | Nakano et al. | |
| 2007/0278938 A1* | 12/2007 | Yabunouchi | C07D 307/91 313/504 |
| 2009/0017331 A1* | 1/2009 | Iwakuma | C09K 11/06 428/690 |
| 2010/0001636 A1 | 1/2010 | Yabunouchi | |
| 2011/0168992 A1 | 7/2011 | Bae et al. | |
| 2011/0278551 A1 | 11/2011 | Yabunouchi et al. | |
| 2011/0315965 A1 | 12/2011 | Takashima et al. | |
| 2012/0119197 A1 | 5/2012 | Nishimura et al. | |
| 2012/0146014 A1 | 6/2012 | Kato | |
| 2012/0248426 A1* | 10/2012 | Kato | C07D 209/86 257/40 |
| 2013/0105771 A1* | 5/2013 | Ryu | C09K 11/06 257/40 |
| 2014/0027747 A1 | 1/2014 | Mun et al. | |

FOREIGN PATENT DOCUMENTS

| | | | |
|---|---|---|---|
| CN | 102482215 A | | 5/2012 |
| EP | 1 146 574 A2 | | 10/2001 |
| EP | 1892776 A2 | | 2/2008 |
| EP | 2011790 A1 | | 1/2009 |
| EP | 2166583 A1 | | 3/2010 |
| JP | 2006-151844 A | | 6/2006 |
| JP | 2014527021 A | | 10/2014 |
| KR | 10-2008-0104025 A | | 11/2008 |
| KR | 10-2011-0011647 | | 2/2011 |
| KR | 10-1029082 B1 | | 4/2011 |
| TW | 201129546 A1 | | 9/2011 |
| TW | 201213497 A1 | | 4/2012 |
| WO | 2007/125714 | † | 11/2007 |
| WO | 2007/125714 A1 | | 11/2007 |
| WO | WO 2007/125714 A1 | * | 11/2007 |
| WO | 2009/145016 | † | 12/2009 |
| WO | 2009/145016 A1 | | 12/2009 |
| WO | 2010061824 A1 | | 6/2010 |
| WO | 2010/074087 A1 | | 7/2010 |
| WO | 2010-074087 A1 | | 7/2010 |
| WO | 2010074087 A1 | | 7/2010 |
| WO | 2011/021520 | † | 2/2011 |
| WO | 2011021520 A1 | | 2/2011 |
| WO | 2011/005099 A1 | | 5/2011 |
| WO | 2011-059099 A1 | | 5/2011 |
| WO | 2011059099 A1 | | 5/2011 |
| WO | WO 2011/133007 A2 | * | 10/2011 |

OTHER PUBLICATIONS

Huang, Tai-Hsiang, et al., "Organic electroluminescent derivatives containing dibenzothiophene and diarylamine segments", Journal of Materials Chemistry, 2002, 15, p. 3233-3240.

\* cited by examiner
† cited by third party

MATERIAL FOR ORGANIC LIGHT-EMITTING DEVICE, AND ORGANIC LIGHT-EMITTING DEVICE USING SAME

This application is a National Stage Application of International Patent Application No. PCT/KR2012/007183, filed on Sep. 6, 2012, which claims priority to and the benefit of Korean Patent Application No. 10-2011-0091943, filed on Sep. 9, 2011 in the Korean Intellectual Property Office, all of which are hereby incorporated by reference.

TECHNICAL FIELD

This application claims priority from Korean Patent Application No. 10-2011-0091943, filed on Sep. 9, 2011 at the KIPO, the disclosure of which is incorporated herein by reference in its entirety.

The present invention relates to a dibenzothiophene-based compound that may significantly improve the service life, efficiency, electrochemical stability and thermal stability of an organic light emitting device, and an organic light emitting device containing the compound in an organic compound layer.

BACKGROUND ART

An organic light emission phenomenon is an example of converting electric current into visible rays through an internal process of a specific organic molecule. The principle of the organic light emission phenomenon is based on the following mechanism. When an organic material layer is disposed between an anode and a cathode, electrons and holes are injected from the cathode and the anode, respectively, into the organic material layer if voltage is applied between the two electrodes. The electrons and the holes which are injected into the organic material layer are recombined to form an exciton, and the exciton is reduced to a bottom state to emit light. The organic light emitting device using the principle may be generally constituted by a cathode, an anode, and an organic material layer that is interposed therebetween, for example, an organic material layer that includes a hole injection layer, a hole transporting layer, a light emitting layer and an electron transporting layer.

The materials used in the organic light emitting device are mostly pure organic materials or complexes of organic materials with metals, and may be classified into a hole injection material, a hole transporting material, a light emitting material, an electron transporting material, an electron injection material and the like, according to the use thereof. Here, an organic material having a p-type property, that is, an organic material which is easily oxidized and electrochemically stable when the material is oxidized, is usually used as the hole injection material or the hole transporting material. Meanwhile, an organic material having an n-type property, that is, an organic material which is easily reduced and electrochemically stable when the material is reduced, is usually used as the hole injection material or the hole transporting material. As the light emitting layer material, an organic material having both p-type and n-type properties is preferred, which is stable when the material is oxidized and when the material is reduced. When an exciton is formed, a material having high light emission efficiency for converting the exciton into light is preferred.

In addition to what is mentioned above, it is preferred that the material used in the organic light emitting device further has the following properties.

First, it is preferred that the material used in the organic light emitting device has excellent thermal stability. The reason is that joule heat is generated by movement of electric charges in the organic light emitting device. NPB, which has currently been used as the hole transporting layer material, has a glass transition temperature of 100° C. or lower, and thus it is difficult to apply to an organic light emitting device requiring a high electric current.

Second, in order to obtain an organic light emitting device that is capable of being driven at low voltage and has high efficiency, holes or electrons which are injected into the organic light emitting device need to be smoothly transported to a light emitting layer, and simultaneously the injected holes and electrons need to be prevented from being released out of the light emitting layer. For this purpose, a material used in the organic light emitting device needs to have an appropriate band gap and appropriate HOMO and LUMO energy levels. A LUMO energy level of PEDOT: PSS, which is currently used as a hole transporting material in an organic light emitting device prepared by a solution coating method, is lower than that of an organic material used as a light emitting layer material, and thus it is difficult to prepare an organic light emitting device having high efficiency and a long service life.

Moreover, the material used in the organic light emitting device needs to have excellent chemical stability, electric charge mobility, interfacial characteristic with an electrode or an adjacent layer, and the like. That is, the material used in the organic light emitting device needs to be minimally deformed by moisture or oxygen.

Furthermore, an appropriate hole or electron mobility needs to be assured so as to balance densities of the holes and of the electrons in the light emitting layer of the organic light emitting device to maximize the formation of excitons. Additionally, it needs to be able to have a good interface with an electrode including metal or metal oxides so as to assure stability of the device.

Accordingly, there is need for developing organic materials having the above-described requirements in the art.

RELATED ART DOCUMENT

Patent Document

US Patent Application Publication No. 2003-0044518
European Patent Application Publication No. 1146574 A2

DISCLOSURE

Technical Problem

The present invention has been made in an effort to provide a hetero compound derivative that may satisfy conditions required in a material available in the organic light emitting device, for example, appropriate energy level, electrochemical stability, thermal stability and the like, and has a chemical structure that may serve various roles required in the organic light emitting device depending on the substituent, and an organic light emitting device including the same.

Technical Solution

The present invention provides a dibenzothiophene-based compound represented by the following Formula 1.

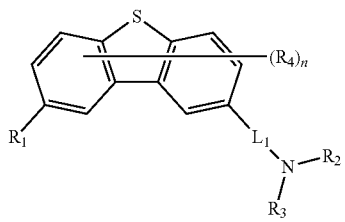

[Formula 1]

in Formula 1, $L_1$ is an arylene group having 6 to 40 carbon atoms; or a fluorenylene group substituted with an alkyl group, $R_1$ is hydrogen; an alkyl group having 1 to 20 carbon atoms; an alkoxy group having 1 to 20 carbon atoms; or an aryl group having 6 to 12 carbon atoms, which is unsubstituted or substituted with an alkyl group having 1 to 20 carbon atoms or an alkoxy group having 1 to 20 carbon atoms, $R_2$ and $R_3$ are the same as each other, and are each an aryl group having 10 to 16 ring-membered carbon atoms, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group; a carbazole group unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group; a thiophenyl group unsubstituted or unsubstituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group; or a heterocyclic group including one or more of N, S and O atoms and having 5 to 12 ring-membered carbon atoms, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group, $R_4$ is hydrogen; an alkyl group having 1 to 20 carbon atoms; or an alkoxy group having 1 to 20 carbon atoms, and may form an aliphatic, aromatic or hetero condensed ring with an adjacent group, and n means the number of substituents and is an integer of 1 to 6.

Further, the present invention provides an organic light emitting device including an organic material layer composed of one more layers including a first electrode, a second electrode and a light emitting layer disposed between the first electrode and the second electrode, in which one or more layers of the organic material layer include the dibenzothiophene-based compound of Formula 1 or a compound in which a heat curable or photo curable functional group is introduced into the dibenzothiophene-based compound.

Advantageous Effects

A compound of the present invention may be used as an organic material layer material, particularly, a hole injection material and/or a hole transporting material in an organic light emitting device, and when the compound is used in the organic light emitting device, the driving voltage of the device may be reduced, light efficiency may be improved, and a service life characteristic of the device may be improved by thermal stability of the compound.

BEST MODE

Figure 1:
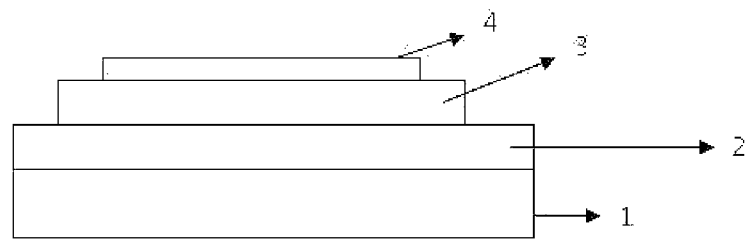
FIG. 1 illustrates an example of an organic light emitting device including a substrate 1, an anode 2, a light emitting layer 3 and a cathode 4.

The present invention provides a dibenzothiophene-based compound represented by the following Formula 1.

In the present invention, the number of ring-membered carbon atoms means the number of carbons constituting an aliphatic ring or an aromatic ring, and when the ring is substituted, the above-described number includes all of the number of ring-membered carbons of the substituent.

Further, the present invention provides an organic light emitting device including an organic material layer composed of one more layers including a first electrode, a second electrode and a light emitting layer disposed between the first electrode and the second electrode, in which one or more layers of the organic material layer include the dibenzothiophene-based compound of Formula 1 or a compound in which a heat curable or photo curable functional group is introduced into the dibenzothiophene-based compound.

Examples of the substituents will be described below, but are not limited thereto.

In the present invention, the alkyl group may be a straight chain or a branched chain, and the number of carbons is 1 to 20. Specific examples thereof include a methyl group, an ethyl group, a propyl group, an isopropyl group, a butyl group, a t-butyl group, a pentyl group, a hexyl group, a heptyl group and the like, but are not limited thereto.

In the present invention, the alkoxy group may be a straight chain or a branched chain, and the number of carbon atoms is 1 to 20.

In the present invention, the alkenyl group may be a straight chain or a branched chain, the number of carbons is not particularly limited, but the number of carbon atoms of the alkenyl group in an embodiment of the present invention is 2 to 20. Specific examples thereof include an alkenyl group which is substituted with an aryl group such as a stylbenyl group, a styrenyl group and the like, but are not limited thereto.

In the present invention, an aryl group of R1 in Formula 1 may be monocyclic or polycyclic, and the number of carbon atoms is 6 to 12. Specific examples of the aryl group include a monocyclic aromatic group, such as a phenyl group, a biphenyl group, a triphenyl group and the like; and a polycyclic aromatic group, such as a naphthyl group and the like, but are not limited thereto.

In the present invention, an arylene group of and a fluorenylene group of $L_1$ in Formula 1 are each a divalent group of an aryl group and a fluorenyl group.

In the present invention, an aryl group in the arylene group of $L_1$ may be monocyclic or polycyclic, and the number of carbon atoms is not particularly limited but is preferably 6 to 60. Specific examples of the aryl group include a monocyclic aromatic group, such as a phenyl group, a biphenyl group, a triphenyl group, a terphenyl group, a stilbene group and the like and a polycyclic aromatic group, such as a naphthyl group, a binaphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, a fluoranthene group and the like, but are not limited thereto.

In the present invention, the fluorenyl group is a structure in which two cyclic organic compounds are linked to each other through one atom, and examples thereof include

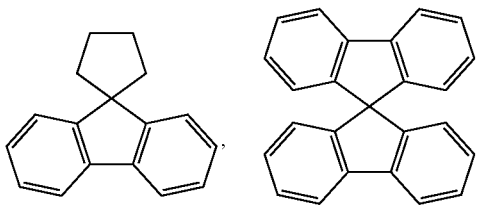

and the like.

In the present invention, the fluorenyl group includes a structure of an open fluorenyl group, and the open fluorenyl group herein is a structure in which two cyclic compounds are linked to each other through one atom and the connection of one cyclic compound is broken, and examples thereof include

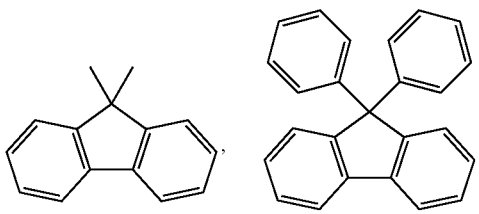

and the like.

In the present invention, the aryl group of $R_2$ and $R_3$ in Formula 1 may be monocyclic or polycyclic, and the number of carbon atoms is 10 to 16. Specific examples of the aryl group include a monocyclic aromatic group, such as a biphenyl group, a stilbene group and the like; and a polycyclic aromatic group, such as a naphthyl group, an anthracenyl group, a phenanthrenyl group, a pyrenyl group, a fluorenyl group, a fluoranthene group and the like, but are not limited thereto.

In the present invention, the hetero ring groups of $R_2$ and $R_3$ in Formula 1 is a heterocyclic group that includes O, N or S as a heteroatom, and the number of carbon atoms is preferably 5 to 12. Examples of the heterocyclic group include a thiophene group, a furan group, a pyrole group, an imidazole group, a thiazole group, an oxazole group, an oxadiazole group, a triazole group, a pyridyl group, a bipyridyl group, a triazine group, an acrydyl group, a pyridazine group, a quinolinyl group, an isoquinoline group, an indol group, a carbazole group, a benzoxazole group, a benzimidazole group, a benzthiazole group, a benzcarbazole group, a benzthiophene group, a dibenzothiophene group, a benzfuranyl group, a phenathroline group, a dibenzofuranyl group and the like, but are not limited thereto.

In one embodiment of the present invention, $L_1$ is an arylene group or a fluorenylene group substituted with an alkyl group.

In one embodiment, $L_1$ is a phenylene group, a biphenylene group or a fluorenylene group substituted with an alkyl group.

In one embodiment, $L_1$ is a phenylene group.

In one embodiment, $L_1$ is a biphenylene group.

In another example, $L_1$ is a fluorenylene group substituted with a methyl group.

In another embodiment, $R_1$ is the hydrogen, an alkyl group having 1 to 20 carbon atoms, an alkoxy group having 1 to 20 carbon atoms or an aryl group unsubstituted or substituted with an alkyl group having 1 to 20 carbon atoms or an alkoxy group having 1 to 20 carbon atoms.

In one embodiment, $R_1$ is hydrogen, or a phenyl group unsubstituted or substituted with an alkyl group having 1 to 20 carbon atoms.

In another embodiment, $R_1$ is hydrogen.

In one embodiment, $R_1$ is an aryl group unsubstituted or substituted with an alkyl group having 1 to 20 carbon atoms.

In one embodiment, $R_1$ is a phenyl group or a biphenyl group.

In another example, $R_1$ is a phenyl group substituted with an alkyl group or a biphenyl group substituted with an alkyl group.

In another example, $R_1$ is a phenyl group substituted with a methyl group or a biphenyl group substituted with a methyl group.

In another example, $R_1$ is a phenyl group.

In one embodiment of the present invention, $R_1$ is an aryl group unsubstituted or substituted with an alkyl group having 1 to 20 carbon atoms or an alkoxy group having 1 to 20 carbon atoms. When $R_1$ is an aryl group substituted with an aryl amine group, the planarity of the entire compound is extremely lowered, thereby making it easy to crystallize the compound, and thus it is difficult for a stable amorphous film to be formed and the electron donor effect of dibenzothiophene on a linked amine group is reduced by half due to the added amine group and as a result, it is difficult to expect that holes are efficiently injected and/or transferred into the light-emitting layer.

In another embodiment, $R_4$ is hydrogen.

In another embodiment, $R_2$ and $R_3$ are the same as each other, and are each an aryl group having 10 to 16 ring-membered carbon atoms, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group.

In another embodiment, $R_2$ and $R_3$ are the same as each other, and are each a biphenyl group, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a nitrile group and a nitro group, or a phenyl group which is substituted with one or more substituents selected from the group consisting of a thiophene group unsubstituted or substituted with a phenyl group and a benzothiophene group.

In another embodiment, $R_2$ and $R_3$ are the same as each other and are a biphenyl group.

In another embodiment, $R_2$ and $R_3$ are the same as each other and are a phenyl group substituted with benzothiophene.

In another embodiment, $R_2$ and $R_3$ are the same as each other and are a phenyl group substituted with a thiophene group substituted with a phenyl group.

In another embodiment, $R_2$ and $R_3$ are the same as each other and are a substituted phenyl group, and the substituted phenyl group is

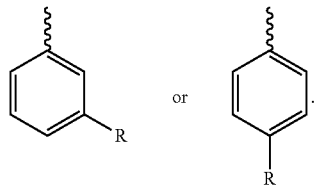

The above-described ∼∼∼ is linked to N in Formula 1, and R is one or more substituents selected from the group consisting of hydrogen, an alkyl group having 1 to 20 carbon atoms, an alkenyl group having 2 to 20 carbon atoms, an alkoxy group having 1 to 20 carbon atoms, a fluorenyl group, a carbazole group, a nitrile group and a nitro group.

In an embodiment of the present invention, R is a benzothiophene group.

In one embodiment of the present invention, R is a substituted thiophene group.

In another example, R is a thiophene group substituted with a phenyl group.

In one embodiment of the present invention, $L_1$ is a phenylene group, a biphenylen group or a fluorenylene group substituted with an alkyl group, $R_1$ is hydrogen, or a phenyl group unsubstituted or substituted with an alkyl group having 1 to 20 carbon atoms, and $R_2$ and $R_3$ are the same as each other, and are each a biphenyl group, a phenyl group substituted with a thiophene group unsubstituted or substituted with a phenyl group, or a phenyl group substituted with benzothiophene.

Formula 1 provides a dibenzothiophene-based compound that is any one of the following Formulas 1-1 to 1-9.

[Formula 1-1]

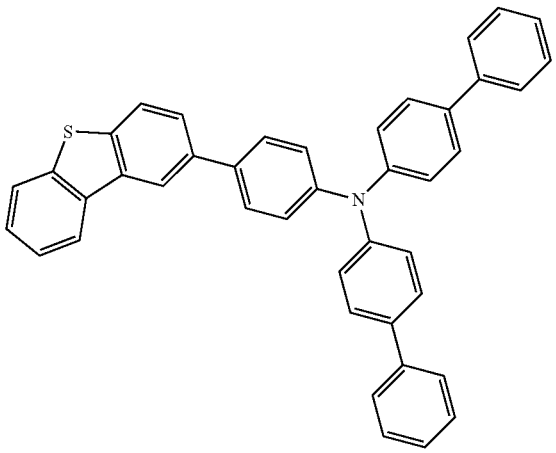

[Formula 1-2]

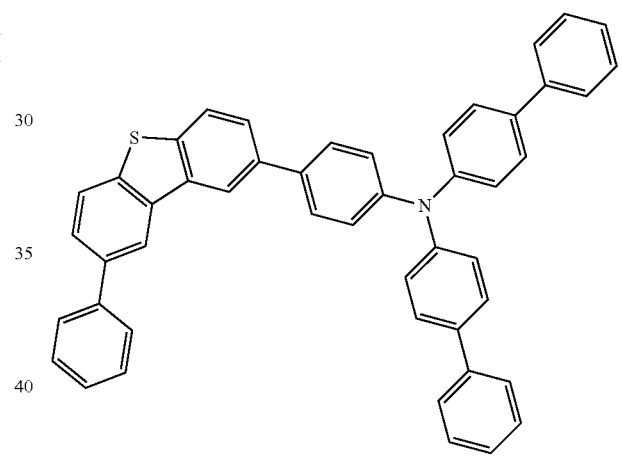

[Formula 1-3]

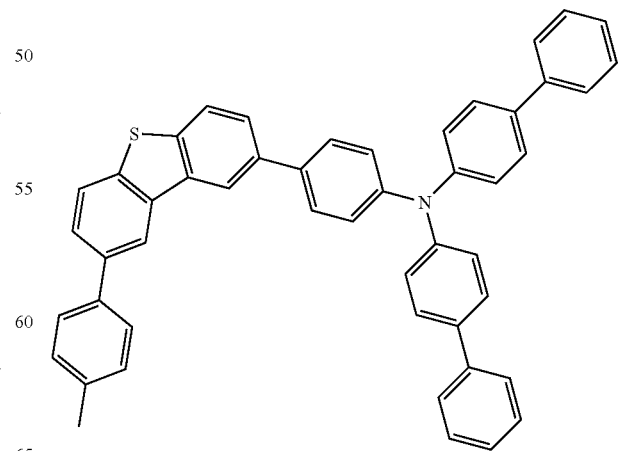

[Formula 1-4]

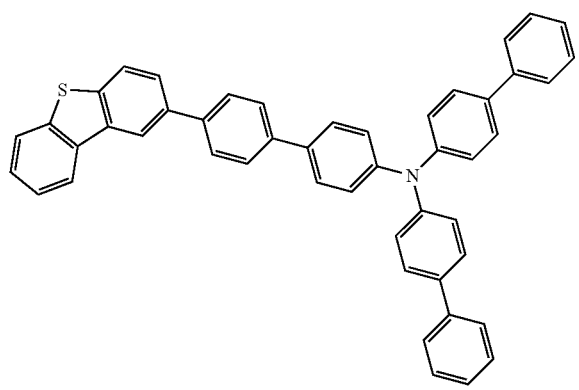

[Formula 1-5]

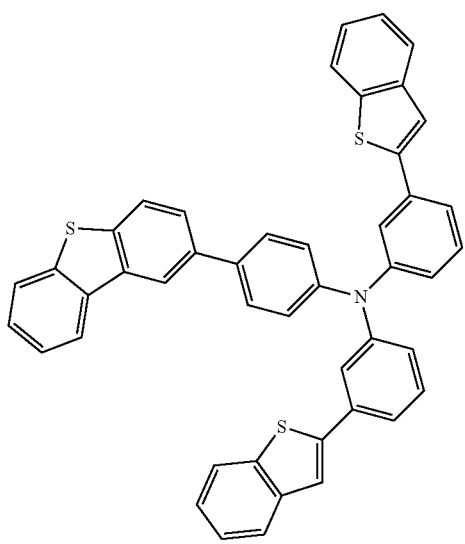

[Formula 1-6]

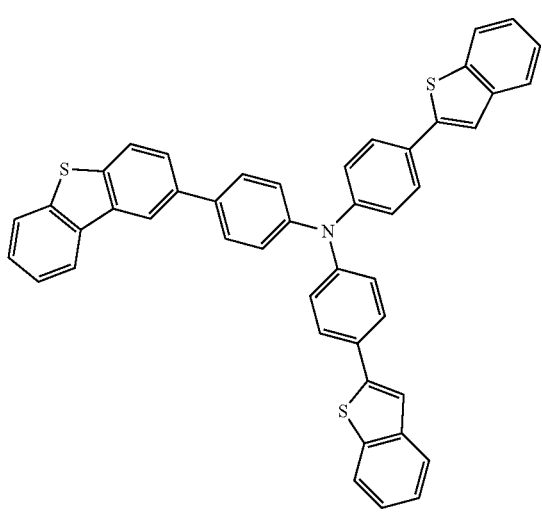

[Formula 1-7]

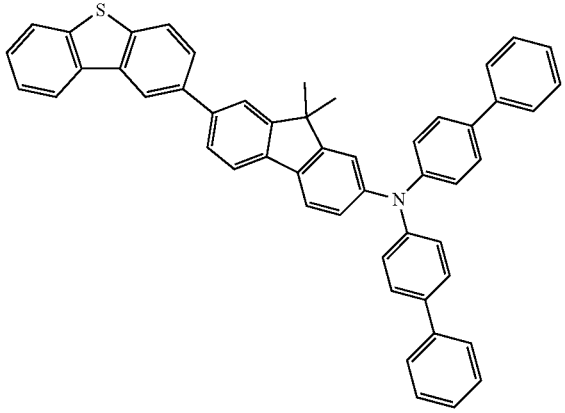

[Formula 1-8]

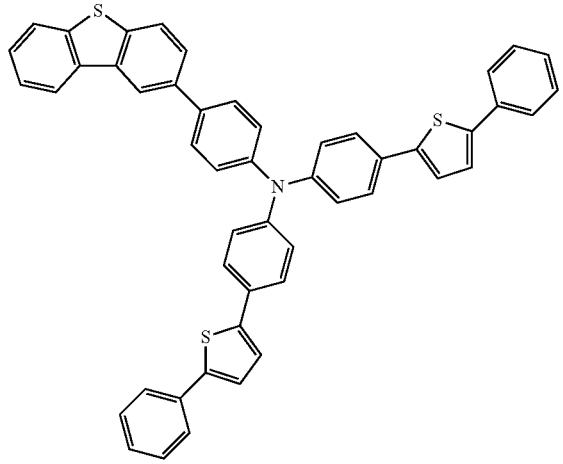

[Formula 1-9]

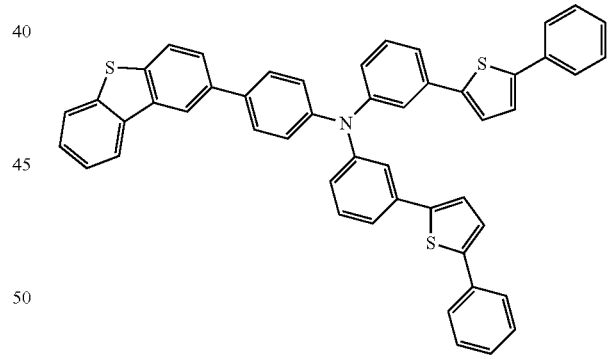

Hereinafter, the present invention will be described in detail.

For the dibenzothiophene-based compound of Formula 1, substituted or unsubstituted dibenzothiophene is substituted with $L_1$ to produce an intermediate. Thereafter, the compound is prepared by a method for substituting the intermediate with $—NR_2R_3$.

The conjugation length of the compound has a close relationship with an energy band gap. Specifically, the energy band gap is reduced as the conjugation length of the compound increases. As described above, the core of the compounds of Formula 1 includes a limited conjugation, and thus the core has properties of a large energy band gap.

In the present invention, compounds having various energy band gaps may be synthesized by introducing various substituents into the positions of $R_1$ to $R_4$ of the core structure having a large energy band gap as described above. It is usually easy to control the energy band gap by introducing a substituent into a core structure having a large energy band gap, but when the core structure has a small energy band gap, it is difficult to increase and control the energy band gap by introducing the substituent. Further, in the present invention, the HOMO and LUMO energy levels of a compound may be controlled by introducing various substituents into the positions of $R_1$ to $R_4$ of the core structure as described above.

In addition, a compound having intrinsic properties of a substituent introduced may be synthesized by introducing various substituents into the core structure as described above. For example, materials satisfying conditions required in each organic material layer may be synthesized by introducing substituents in a hole injection layer material, a hole transporting layer material, a light emitting layer material and an electron transporting layer material used during the preparation of an organic light emitting device into the core structure.

The compound of Formula 1 includes an amine structure linked to the core structure through an arylene group, and thus the organic light emitting device may have an appropriate energy level as a hole injection and/or hole transporting material. In the present invention, a device having a low driving voltage and a high light efficiency may be implemented by selecting a compound having an appropriate energy level depending on the substituent among the compounds of Formula 1 and using the compound in an organic light emitting device.

Furthermore, it is possible to finely control the energy band gap by introducing various substituents into the core structure, and meanwhile characteristics at the interface between organic materials are improved, thereby making it possible to use the material in various fields. Further, it is possible to finely control the HOMO and LUMO energy levels and the energy band gap, and meanwhile, characteristics at the interface between organic materials are improved, thereby making it possible to use the material in various fields.

Meanwhile, the compound of Formula 1 has a high glass transition temperature (Tg), and thus has excellent thermal stability. The improvement in thermal stability is an important factor which provides the driving stability to a device and a long service-life device.

In addition, when $R_2$ and $R_3$ have the same substituent in Formula 1, the LUMO distribution is not distributed throughout the molecule or at $R_2$ and $R_3$, which are substituents bonded to a nitrogen atom due to the relative symmetry thereof, but locally concentrated at dibenzothiophene. As a result, it is possible to obtain an effect that the band gap is wide and triplet energy $T_1$ is high.

According to one embodiment of the present invention, when a compound having a wide band gap and high triplet energy is used as a hole transfer layer or a host material, singlet and triplet excitons produced in a light emitting layer are shut in the light emitting layer, and thus an effect of improving the electric current efficiency may be obtained.

In one embodiment according to the present invention, $R_2$ and $R_3$ of Formula 1 are an aryl group having 10 to 16 ring-membered carbon atoms.

When the number of ring-membered carbon atoms is less than 10, there is a problem in thermal stability due to the glass transition temperature (Tg) depending on the low molecular weight.

In one embodiment of the present invention, when the number of ring-membered carbon atoms is 10 to 16, an appropriate HOMO level may be obtained to increase the hole injection efficiency in the light emitting layer and the molecular weight of the entire compound is appropriate, and thus a stable amorphous film, with which it is difficult to achieve crystallization, is formed.

Furthermore, in Formula 1, when $L_1$ in the following dibenzothiophene structure is linked to the 11th position of dibenzothiophene, the electron donor effect of dibenzothiophene on a linked amine group may be improved more than when $L_1$ is linked to the 13th position that is close to the sulfur element of dibenzothiophene, and thus the hole injection into the light emitting layer and the transfer efficiency thereof may be increased, thereby having better characteristics in terms of voltage and efficiency.

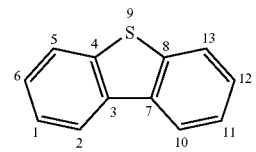

Further, an exemplary embodiment of the present invention provides an organic light emitting device including an organic material layer composed of one more layers including a first electrode, a second electrode and a light emitting layer disposed between the first electrode and the second electrode, in which one or more layers of the organic material layer include the compound of Formula 1 or a compound in which a heat curable or photo curable functional group is introduced into the compound.

In the organic light emitting device according to the present invention, the compound according to the present invention may be used as a hole injection material, a hole transporting material, a light emitting material, an electron transporting material, an electron injection material and the like, and more preferably used as a hole transporting material.

The organic material layer of the organic light emitting device of the present invention may be composed of a mono-layer structure, but may be composed of a multi-layer structure in which organic material layers having two or more layers are stacked. For example, the organic light emitting device of the present invention may have a structure include a hole injection layer, a hole transporting layer, a light emitting layer, an electron transporting layer, an electron injection layer and the like as an organic material layer. However, the structure of the organic light emitting device is not limited thereto, and may include a fewer number of organic material layers.

Figure 2:
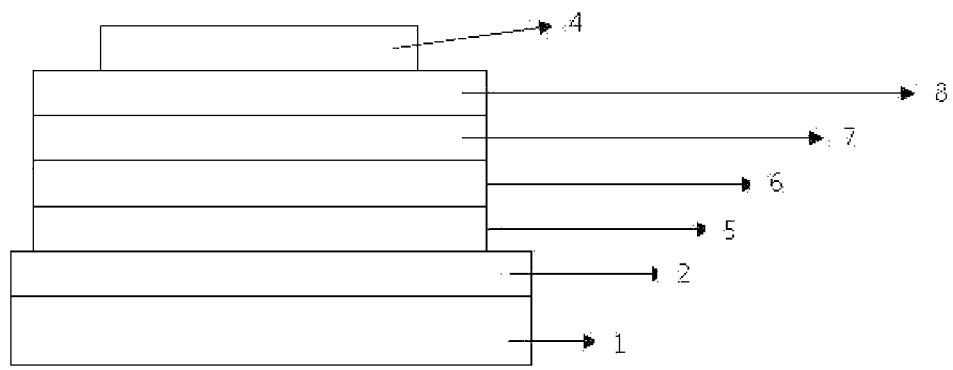
FIG. 2 illustrates an example of an organic light emitting device including a substrate 1, an anode 2, a hole injection layer 5, a hole transporting layer 6, a light emitting layer 7, an electron transporting layer 8 and a cathode 4.

The organic light emitting device of the present invention may have structures as shown in FIGS. 1 and 2, but is not limited thereto.

FIG. 1 illustrates a structure of an organic light emitting device in which a substrate 1, an anode 2, a light emitting layer 3 and a cathode 4 are sequentially stacked. In the structure, the compound may be included in the light emitting layer 3.

FIG. 2 illustrates a structure of an organic light emitting device in which a substrate 1, an anode 2, a hole injection layer 5, a hole transporting layer 6, a light emitting layer 7, an electron transporting layer 8 and a cathode 4 are sequentially stacked. In the structure, the compound may be included in one or more of the hole injection layer 5, the hole transporting layer 6, the light emitting layer 7 and the electron transporting layer 8.

One embodiment of the present invention provides an organic light emitting device, in which the organic material layer includes a hole transporting layer and the hole transporting layer includes the dibenzothiophene-based compound or a compound in which a heat curable or photo curable functional group is introduced into the dibenzothiophene-based compound.

One embodiment of the present invention provides an organic light emitting device, in which the organic material layer includes a two-layered hole transporting layer and at least one layer of the hole transporting layer includes the compound represented by Formula 1 or a compound in which a heat curable or photo curable functional group is introduced into the compound represented by Formula 1.

In another embodiment, the organic material layer includes a first hole transporting layer and a second hole transporting layer, and the first hole transporting layer includes the benzothiophene-based compound or a compound in which a heat curable or photo curable functional group is introduced into the dibenzothiophene-based compound, and in the second hole transporting layer, an aromatic amine compound is used. As the aromatic amine compound, monoamine, diamine, triamine and tetramine are used. Specific examples of the aromatic amine compound include 4,4'-bis[N-(1-naphthyl)-N-phenyl-amino]-biphenyl (α-NPD), 4,4'-bis[N-(3-methylphenyl)-N-phenyl-amino]-biphenyl (TPD), 4,4',4"-tris(N,N-diphenyl-amino)-triphenylamine (TDATA), 4,4',4"-tris[N-(3-methylphenyl)-N-phenyl-amino]-triphenylamine (MTDATA) and the like, but are not limited thereto.

In the present invention, when a light emitting layer is formed by using a host material having a wide energy gap in an organic light emitting device including two or more layers of the hole transporting layer, the difference between the ionization potential (IP) of the host material and the ionization potential (IP) of the hole injection and hole transporting layer is increased, thereby making it difficult to inject and transport holes into the light emitting layer, and thus there is a concern in that a driving voltage for obtaining sufficient luminance intensity may be increased. Even in this case, the compound of Formula 1 may be used to introduce an assist layer having a hole transporting property, which is in contact with the light emitting layer, that is, a first hole transporting layer, thereby facilitating the transportation of holes into the light emitting layer to reduce the driving voltage. In addition, the first hole transporting layer including the compound of Formula 1 may be designed to have LUMO and triplet energy values higher than those of the host material, and thus blocks electrons and excitons from leaking from the light emitting layer, thereby improving device efficiency and service life characteristics.

Another embodiment provides an organic light emitting device in which the second hole transporting layer is interposed between an anode and a first hole transporting layer.

Another embodiment provides an organic light emitting device in which the first hole transporting layer is interposed between the light emitting layer and the second hole transporting layer.

Another embodiment provides an organic light emitting device in which the first hole transporting layer is in contact with the light emitting layer.

When the first hole transporting layer including the dibenzothiophene-based compound represented by Formula 1 or a compound in which a heat curable or photo curable functional group is introduced into the dibenzothiophene-based compound is brought into contact with the light emitting layer, holes injected from the first electrode effectively moves to the light emitting layer, and if the ratio of the dibenzothiophene-based compound in the hole transporting layer is controlled, the probability of producing excitons in the light emitting layer may be increased and the produced excitons may be controlled to be produced evenly throughout the light emitting layer. In this case, excitons fail to contribute to light emission and are injected into the adjacent electron transporting layer to reduce the probability that excitons emit no light and are extinguished and thus the light emitting efficiency is improved, and excitons are concentrated at one side to prevent the effect of accelerating the aging of the specific portion in the light emitting layer, thereby implementing an organic light emitting device with the service life improved.

Figure 3:
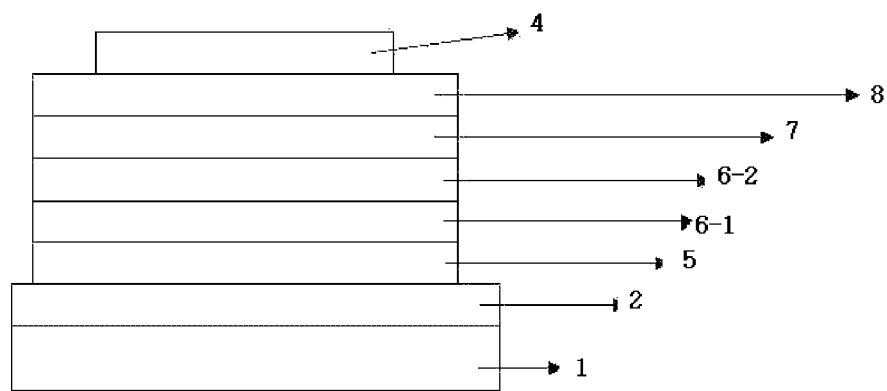
FIG. 3 illustrates an example of an organic light emitting device, in which a substrate 1, an anode 2, a hole injection layer 5, a hole transporting layer 6-1 that does not include a compound represented by Formula 1, a hole transporting layer 6-2 including a compound represented by Formula 1, a light emitting layer 7, an electron transporting layer 8 and a cathode 4 are sequentially stacked.

FIG. 3 illustrates a structure of an organic light emitting device, in which a substrate 1, an anode 2, a hole injection layer 5, a hole transporting layer 6-1 that does not include a compound represented by Formula 1, a hole transporting layer 6-2 including a compound represented by Formula 1, a light emitting layer 7, an electron transporting layer 8 and a cathode 4 are sequentially stacked.

Another embodiment provides an organic light emitting device, in which the organic material layer includes a hole injection layer and the hole injection layer include the above-described compound or a compound in which a heat curable or photo curable functional group is introduced into the compound.

Another embodiment provides an organic light emitting device, in which the organic material layer includes a layer that simultaneously injects and transports holes and the layer includes the above-described compound or a compound in which a heat curable or photo curable functional group is introduced into the compound.

Another embodiment provides an organic light emitting device, in which the organic material layer includes an electron injection and electron transporting layer and the electron injection or electron transporting layer includes the above-described compound or a compound in which a heat curable or photo curable functional group is introduced into the compound.

Another embodiment provides an organic light emitting device, in which the organic material layer includes a light emitting layer and the light emitting layer includes the above-described compound or a compound in which a heat curable or photo curable functional group is introduced into the compound.

Furthermore, the compound of Formula 1 may be formed as an organic material layer by using a vacuum deposition method as well as a solution coating method during the manufacture of an organic light emitting device. Here, the solution coating method means spin coating, dip coating, inkjet printing, screen printing, a spray method, roll coating and the like, but is not limited thereto.

In the organic light emitting device of the present invention, it is possible to use a compound in which a heat curable or photo curable functional group is introduced into the compound of Formula 1 instead of the compound of Formula 1. This kind of compound retains basic physical properties of the above-described compound of Formula 1 and simultaneously may be formed as an organic material layer by a method of forming a thin film by a solution coating method during the manufacture of a device and then curing the thin film.

The method for forming an organic material layer including: introducing a curable functional group into an organic material during the manufacture of an organic light emitting device, forming a thin film of the organic material by a solution coating method, and curing the thin film is described in US Patent Application Publication No. 2003-0044518, European Patent Application Publication No. 1146574 A2 and the like.

In the publications, it is described that when a material having a vinyl group or an acryl group, which is capable of heat curing or photo curing, is used to form an organic material layer by the method as described above, an organic light emitting device having a multi-layer structure may be manufactured by a solution coating method and a low voltage and high luminance organic light emitting device may be manufactured. The principle as described above may also be applied to the compound of the present invention.

In the present invention, the heat curable or photo curable functional group may be a vinyl group, an acryl group or the like.

The organic light emitting device of the present invention may be manufactured by a material and a method known in the art, except that one or more layers of the organic material layer include the compound of the present invention, that is, the compound of Formula 1.

For example, the organic light emitting device of the present invention may be manufactured by sequentially stacking a first electrode, an organic material layer and a second electrode on a substrate. At this time, the organic light emitting device may be manufactured by depositing a metal or a metal oxide having conductivity, or an alloy thereof on a substrate to form an anode by a physical vapor deposition (PVD) method such as sputtering or e-beam evaporation, forming an organic material layer that includes a hole injection layer, a hole transporting layer, a light emitting layer and an electron transporting layer thereon, and then depositing a material that may be used as the cathode thereon. In addition to these methods, an organic light emitting device may be manufactured by sequentially depositing an organic material layer from a cathode material and an anode material on a substrate.

Further, the compound of Formula 1 may be formed as an organic material layer by using a vacuum deposition method as well as a solution coating method during the manufacture of an organic light emitting device. Here, the solution coating method means spin coating, dip coating, doctor blading, inkjet printing, screen printing, a spray method, roll coating and the like, but is not limited thereto.

In one embodiment of the present invention, the first electrode may become an anode and the second electrode may become a cathode.

In another embodiment of the present invention, the first electrode may become a cathode and the second electrode may become an anode.

It is preferred that as the anode material, materials having a high work function are usually used so as to facilitate the injection of holes into the organic material layer. Specific examples of the anode material that may be used in the present invention include metals such as vanadium, chromium, copper, zinc and gold, or alloys thereof; metal oxides such as zinc oxide, indium oxide, indium tin oxide (ITO) and indium zinc oxide (IZO); a combination of metal and oxide, such as $ZnO:Al$ or $SnO_2:Sb$; and electrically conductive polymers, such as poly(3-methylthiophene), poly[3,4-(ethylene-1,2-dioxy)thiophene](PEDOT), polypyrrole and polyaniline, and the like, but are not limited thereto.

It is preferred that as the cathode material, materials having a low work function are usually used so as to facilitate the injection of electrons into the organic material layer. Specific examples of the cathode material include metals such as magnesium, calcium, sodium, potassium, titanium, indium, yttrium, lithium, gadolinium, aluminum, silver, tin and lead, or alloys thereof; multi-layer structured materials such as $LiF/Al$ or $LiO_2/Al$, and the like, but are not limited thereto.

The hole injection material is a material facilitating hole injection from the anode at low voltage, and the highest occupied molecular orbital (HOMO) of the hole injection material is preferably located between the work function of the anode material and the HOMO of the neighboring organic material layer. Specific examples of the hole injection material include metal porphyrine, oligothiophene, arylamine-based organic materials, hexanitrile hexaazatriphenylene-based organic materials, quinacridone-based organic materials, perylene-based organic materials, antraquinone, polyaniline-based and polythiophene-based conductive polymers and the like, but are not limited thereto.

The hole transporting material is suitably a material having high hole mobility, which may accept and transfer holes from the anode or the hole injection layer to the light emitting layer. Specific examples thereof include arylamine-based organic materials, conductive polymers, block copolymers having both conjugated portions and non-conjugated portions and the like, but are not limited thereto.

The light emitting material is a material that is capable of emitting light in a visible ray region by accepting and recombining holes from the hole transporting layer and electrons from the electron transporting layer, respectively, and preferably a material having high quantum efficiency for fluorescence and phosphorescence. Specific examples thereof include 8-hydroxy-quinoline-aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; and polyfluorene, rubrene and the like, but are not limited thereto.

The electron transporting material is suitably a material having high electron mobility, which may accept and transfer electrons from the cathode to the light emitting layer. Specific examples thereof include aluminum complexes of 8-hydroxyquinoline; complexes including $Alq_3$; organic radical compounds; hydroxyflavone-metal complexes, and the like, but are not limited thereto.

The organic light emitting device according to the present invention may be a top emission type, a bottom emission type or a top or bottom emission type according to the materials used.

The compound according to the present invention may apply similar principles, which are applied to organic light emitting devices, to organic light emitting devices including organic solar cells, organic photoconductors, organic transistors and the like.

The synthesizing method of the organic compound represented by Formula 1 and the manufacture of an organic light emitting device using the same will be described in more detail with reference to the following Examples and Comparative Examples. However, these Examples are provided for illustrative purposes only, and the scope of the present invention is not limited only by these.

EXAMPLES

Synthetic Example 1

Preparation of Compound Represented by Formula 1-1

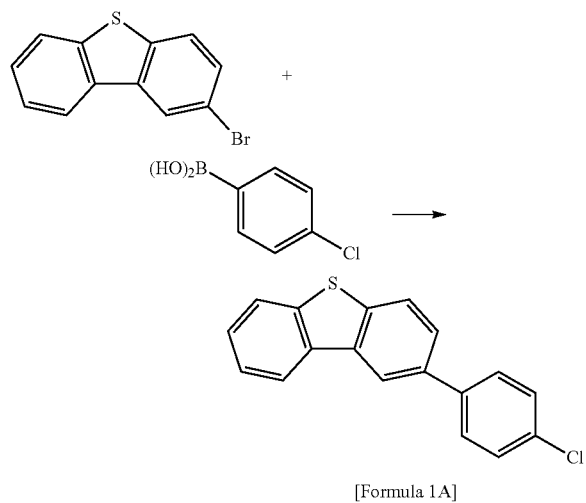

[Formula 1A]

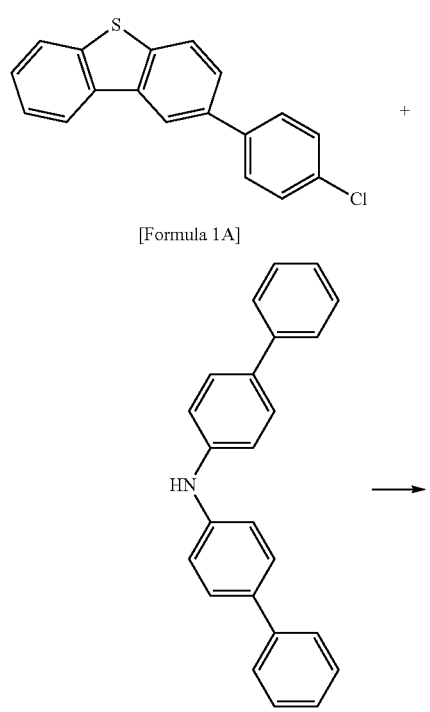

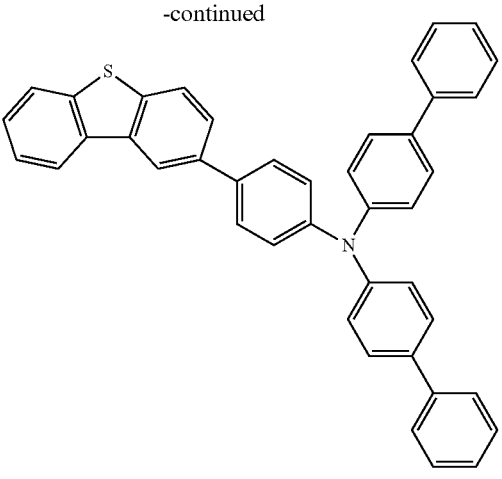

[Formula 1-1]

(1) Preparation of Formula 1A 2-bromodibenzothiophene (30 g, 114 mmol), 4-chlorophenyl boric acid (19.6 g, 125 mmol) and potassium carbonate ($K_2CO_3$) (39.4 g, 285 mmol) were dissolved in tetrahydrofuran (THF) (300 ml) and $H_2O$ (100 ml) and the solution was heated at 50° C. Tetrakis(triphenylphosphine)palladium ($Pd(PPh_3)_4$) (1.3 g, 1.14 mmol) was added thereto and then the mixture was refluxed for 12 hours. The mixture was cooled to normal temperature, and then the water layer was removed. Magnesium sulfate ($MgSO_4$) was put into the organic layer and then the mixture was filtered. The mixture was concentrated, and then was purified by column chromatography to obtain the compound of Formula 1A (20 g, yield 60%).

MS: $[M+H]^+$=294

(2) Preparation of Formula 1-1

The compound of Formula 1A (10 g, 33.9 mmol), bisbiphenyl amine (11.4 g, 35.6 mmol), NaOtBu (4.2 g, 44.1 mmol) and xylene (100 ml) were mixed, and then the mixture was heated at 100° C. Bis[(tri-tertiary-butyl)phosphine]palladium ($Pd(p-t-Bu_3)_2$) (170 mg, 0.34 mmol) was added thereto, and then the mixture was refluxed for 48 hours. The mixture was cooled to normal temperature, and then was purified by column chromatography. The mixture was dried to obtain the compound of Formula 1-1 (5.5 g, yield 28%).

MS: $[M+H]^+$=580

Synthetic Example 2

Preparation of Compound Represented by Formula 1-4

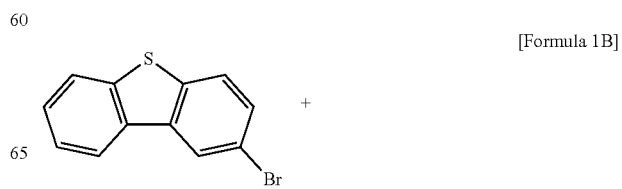

[Formula 1B]

-continued

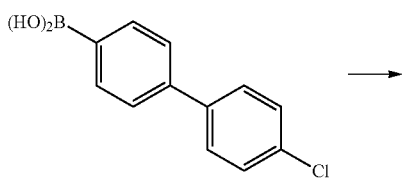

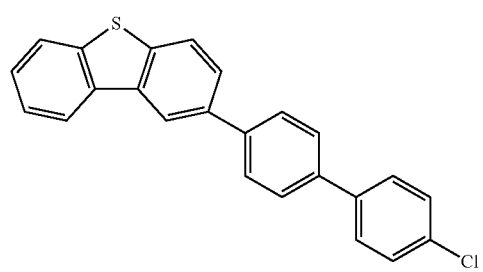

[Formula 1B]

[Formula 1-4]

+

-continued

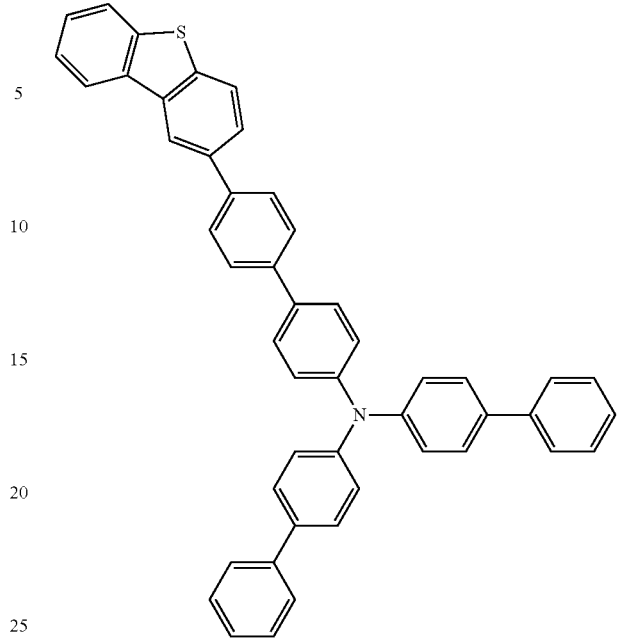

(1) Preparation of Formula 1B

A compound of Formula 1B (25 g, yield 59%) was obtained in the same manner as in the preparation of the compound 1A in Synthetic Example 1, except that a compound 4-chlorobiphenyl boronic acid (25 g, 125 mmol) was used instead of the compound 4-chlorophenyl boronic acid.

MS: $[M+H]^+=371$ (2) Preparation of Formula 1-4

The compound of Formula 1B (10 g, 27 mmol), bisbiphenyl amine (9.1 g, 28.4 mmol), NaOtBu (3.4 g, 35.1 mmol) and xylene (100 ml) were mixed and then the mixture was heated at 100° C. Bis[(tri-tertiary-butyl)phosphine]palladium $(Pd(p-t-Bu_3)_2)$ (138 mg, 0.27 mmol) was added thereto, and then the mixture was refluxed for 48 hours. The mixture was cooled to normal temperature, and then was purified by column chromatography. The mixture was dried to obtain the compound of Formula 1-4 (7 g, yield 40%).

MS: $[M+H]^+=656$

Synthetic Example 3

Preparation of Compound Represented by Formula 1-5

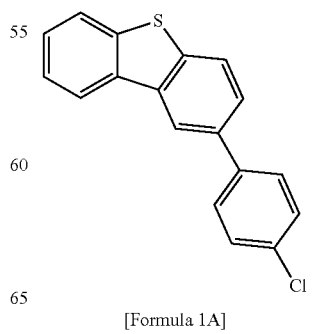

[Formula 1A]

Synthetic Example 4

Preparation of Compound Represented by Formula 1-6

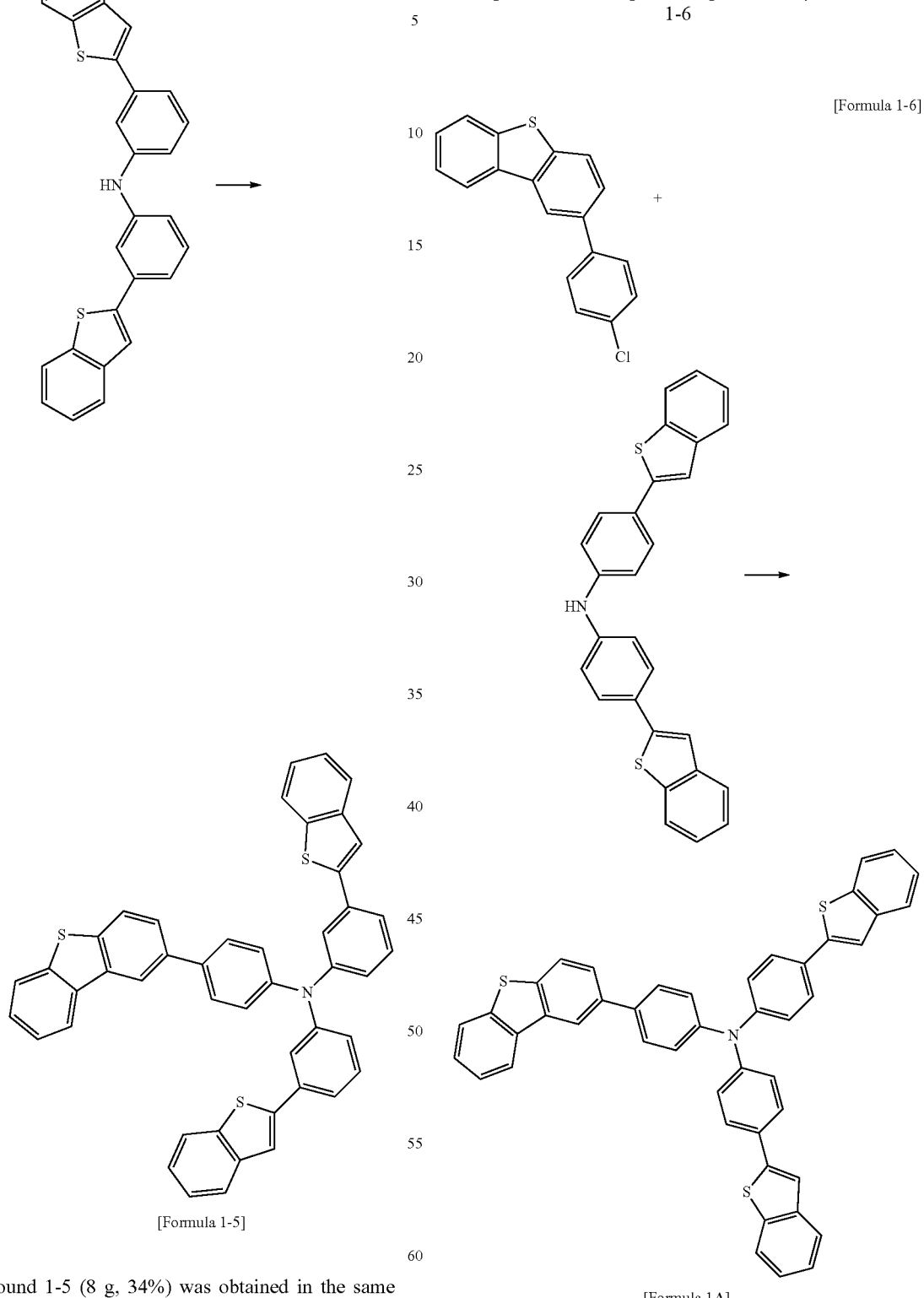

[Formula 1-6]

[Formula 1A]

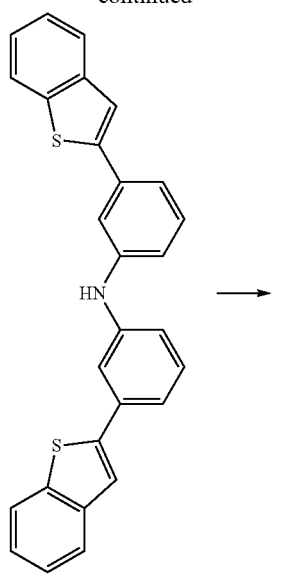

[Formula 1-5]

A compound 1-5 (8 g, 34%) was obtained in the same manner as in the preparation of the compound 1-1 in Synthetic Example 1, except that the compound 4-bis-diphenylbenzothiophene amine (15.4 g, 35.6 mmol) was used instead of the compound bisdiphenylamine.

MS: [M+H]$^+$=692

A compound 1-6 (8.5 g, 36%) was obtained in the same manner as in the preparation of the compound 1-1 in Synthetic Example 1, except that the compound 3-bis-diphenylbenzothiophene amine (15.4 g, 35.6 mmol) was used instead of the compound bisdiphenylamine.

MS: [M+H]⁺=692

Synthetic Example 5

Preparation of Compound Represented by Formula 1-7

[Formula 1C]

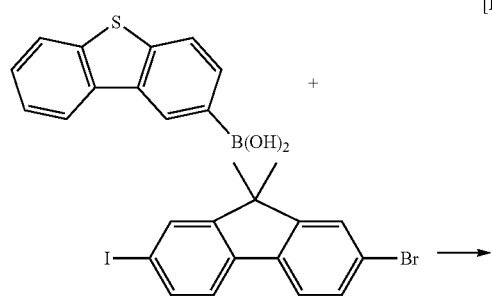

[Formula 1-7]

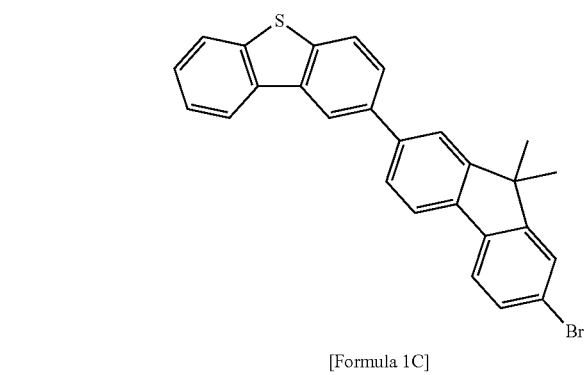

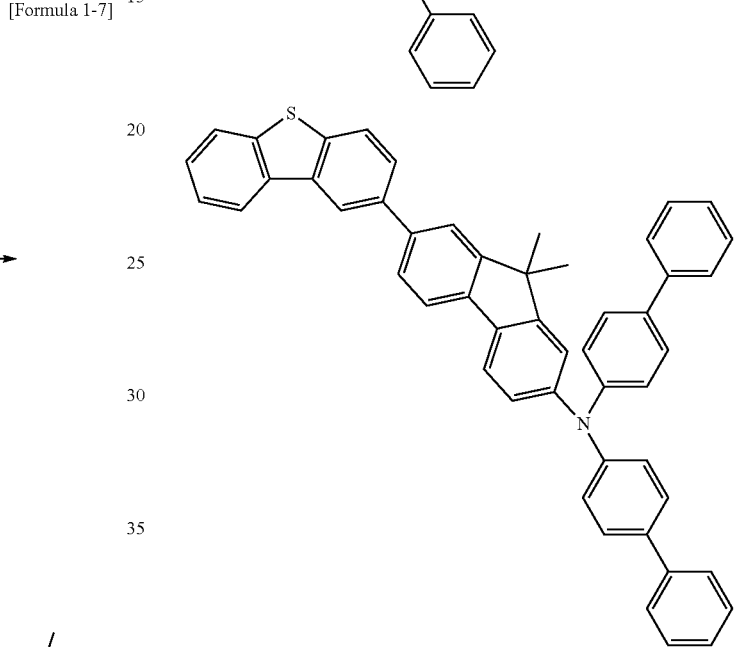

(1) Preparation of Formula 1C 2-dibenzothiophene boronic acid (10 g, 43.9 mmol), 2-bromo-7-iodine-9,9-dimethyl-9H-fluorene (17.5 g, 43.9 mmol) and potassium carbonate ($K_2CO_3$) (18.2 g, 132 mmol) were dissolved in tetrahydrofuran (THF) (300 ml) and water (100 ml) and then the mixture was heated at 50° C. Tetrakis(triphenylphosphine) palladium ($Pd(PPh_3)_4$) (1.0 g, 0.88 mmol) was added thereto and then the mixture was refluxed for 12 hours. The mixture was cooled to normal temperature, and then the water layer was removed. Magnesium sulfate ($MgSO_4$) was put into the organic layer and then the mixture was filtered. The mixture was concentrated, and then was purified by column chromatography to obtain the compound of Formula 1C (15 g, yield 75%).

MS: [M+H]⁺=455

(2) Preparation of Formula 1-7

A compound 1-7 (3.5 g, 49%) was obtained in the same manner as in the preparation of the compound 1-1 in Synthetic Example 1, except that the compound 1C (10 g, 22 mmol) was used instead of the compound 1A.

MS: [M+H]⁺=695

Synthetic Example 6

Preparation of the Compound Represented by Formula 1-8

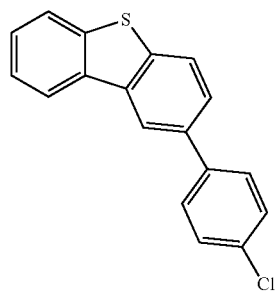

[Formula 1A]

+

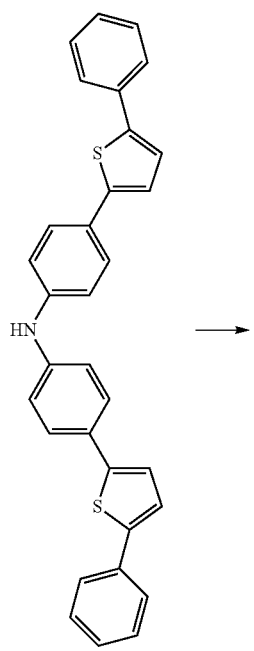

→

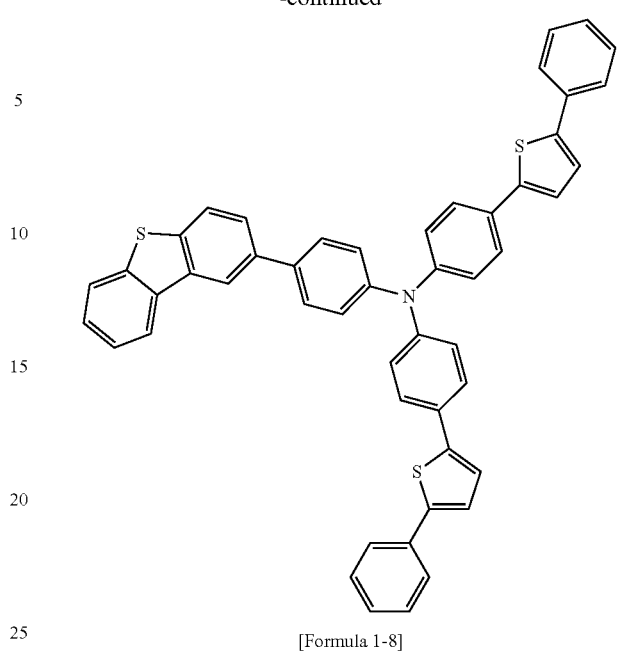

[Formula 1-8]

A compound 1-8 (9.5 g, 38%) was obtained in the same manner as in the preparation of the compound 1-1 in Synthetic Example 1, except that the compound 4-bis-2,5-diphenylthiophene amine (17.3 g, 35.6 mmol) was used instead of the compound bisdiphenylamine.

MS: $[M+H]^+=744$

Synthetic Example 7

Preparation of Compound Represented by Formula 1-9

[Formula 1A]

[Formula 1-9]

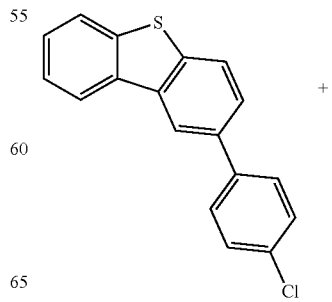

+

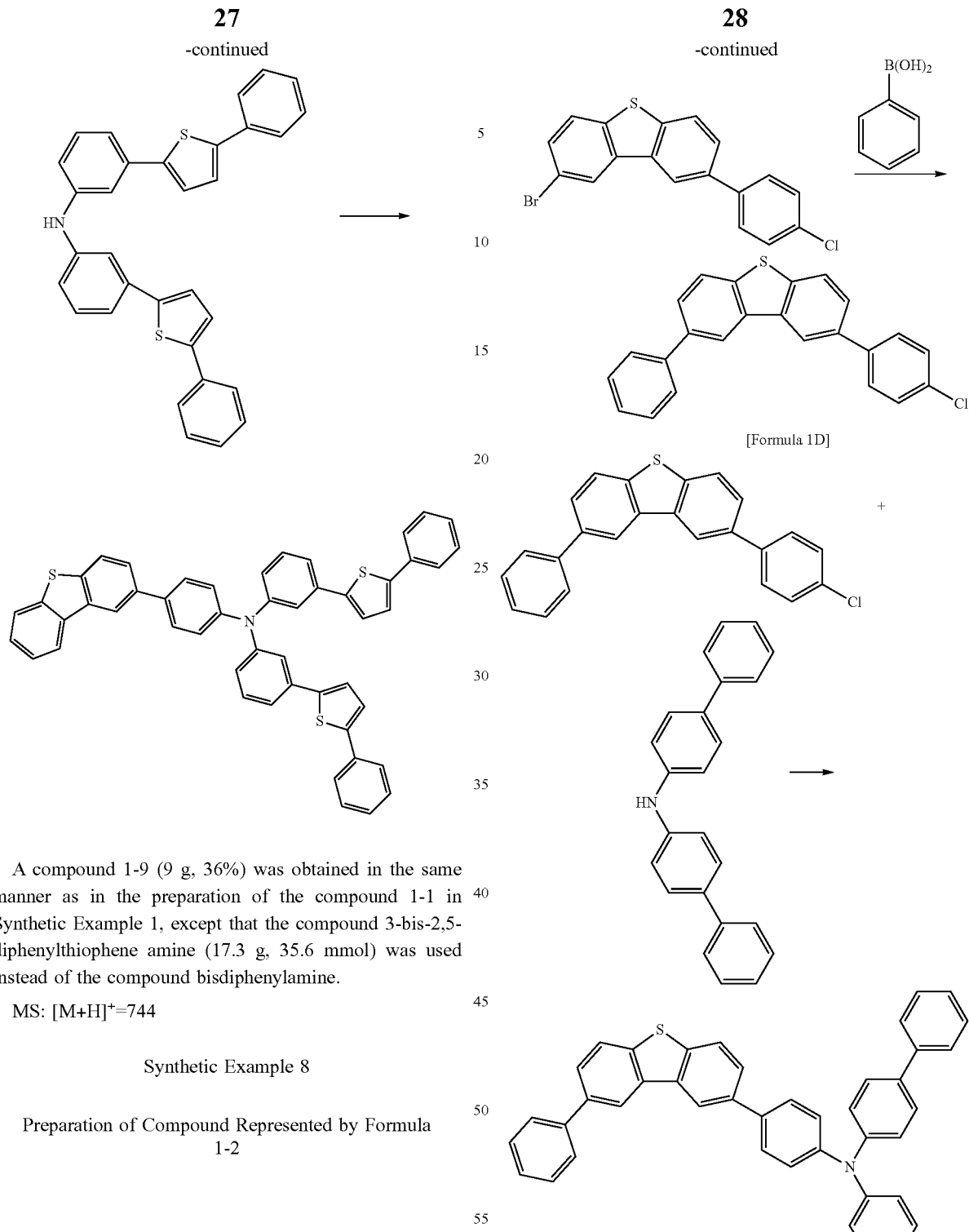

A compound 1-9 (9 g, 36%) was obtained in the same manner as in the preparation of the compound 1-1 in Synthetic Example 1, except that the compound 3-bis-2,5-diphenylthiophene amine (17.3 g, 35.6 mmol) was used instead of the compound bisdiphenylamine.

MS: [M+H]$^+$=744

Synthetic Example 8

Preparation of Compound Represented by Formula 1-2

[Formula 1A]

[Formula 1-2]

(1) Preparation of Formula 1D

The compound 1A (30 g, 102 mmol) was introduced into a flask including 1 L of dichloromethane to dissolve the compound 1A, then a solution in which bromine (5.26 ml, 102 mmol) was diluted with 400 ml of dichloromethane was slowly added dropwise to the flask, and the mixture was stirred for 12 hours. After the reaction was completed, the reactant solution contained in the flask was washed with a sodium hydrogen carbonate saturated aqueous solution, then the organic layer was separated from the flask, dried over anhydrous magnesium sulfate and then filtered. The filtrate was concentrated and then recrystallized with dichloromethane and ethanol to obtain a white solid compound (15.2 g, 40%).

The compound along with phenyl boronic acid (5.5 g, 44.8 mmol) and potassium carbonate ($K_2CO_3$) (16.9 g, 122 mmol) was dissolved in tetrahydrofuran (THF) (400 ml) and water (150 ml) and the solution was heated at 90° C. Tetrakis(triphenylphosphine) palladium ($Pd(PPh_3)_4$) (0.94 g, 0.81 mmol) was added thereto and then the mixture was refluxed for 12 hours. The mixture was cooled to normal temperature, and then the water layer was removed. Magnesium sulfate ($MgSO_4$) was put into the organic layer and then the mixture was filtered. The mixture was concentrated, and then was purified by column chromatography to obtain the Formula 1D (8 g, yield 51%).

MS: $[M+H]^+=371$ (2) Preparation of Formula 1-2

A compound 1-2 (10.6 g, 60%) was obtained in the same manner as in the preparation of the compound 1-1 in Synthetic Example 1, except that the compound 1D (10 g, 27 mmol) was used instead of the compound 1A.

MS: $[M+H]^+=656$

Example 1

A glass substrate (corning 7059 glass), on which ITO (indium tin oxide) was coated to a thickness of 1000 Å to form a thin film, was put in distilled water, in which a dispersing agent was dissolved, and then washed using ultrasonic waves. A product manufactured by Fischer Co. was used as a detergent, and distilled water subjected to secondary filtration with a filter manufactured by Millipore Co. was used. After ITO was washed for 30 minutes, ultrasonic washing was conducted twice by using distilled water for 10 min. After washing using distilled water was completed, ultrasonic washing was conducted using isopropyl alcohol, acetone, and methanol solvents in sequence, and drying was then conducted.

Hexanitrile hexaazatriphenylene was vacuum deposited to a thickness of 500 Å by heating on a transparent ITO electrode, which was thus prepared, so as to form a hole injection layer. The compound of Formula 1-1 (400 Å), which was synthesized above in Synthetic Example 1, as a material for transporting holes was vacuum deposited thereon, and a host H1 and a dopant D1 compound were vacuum deposited to a thickness of 300 Å as a light emitting layer. Next, the E1 compound (300 Å) was vacuum deposited sequentially as an electron injection and transporting layer by heating. An organic light emitting device was manufactured by sequentially depositing lithium fluoride (LiF) having a thickness of 12 Å and aluminum having a thickness of 2000 Å on the electron transporting layer to form a cathode.

In the above-described procedure, the deposition rate of the organic material was maintained at 1 Å/sec, while the deposition rates of lithium fluoride and aluminum were maintained at 0.2 Å/sec and 3 to 7 Å/sec, respectively.

[Hexanitrile hexaazatriphenylene] [HT1]

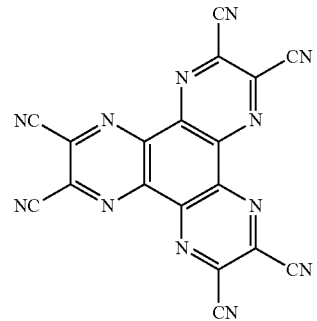

[NPB]

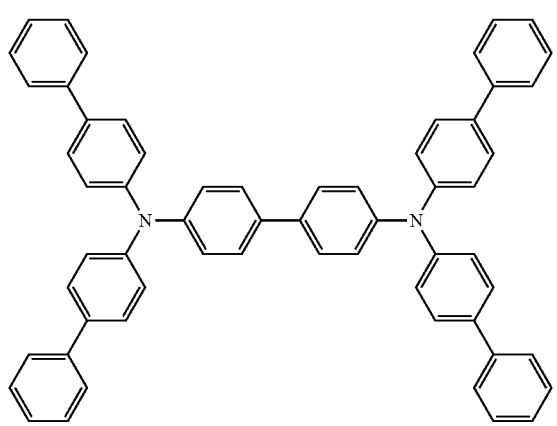

[HT2]

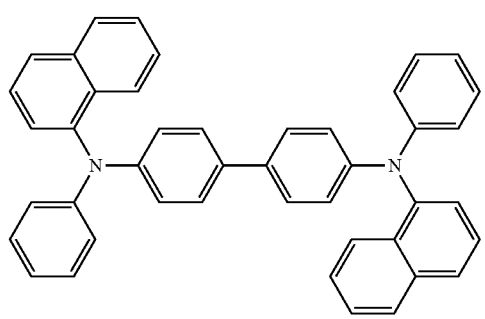

[HT3]

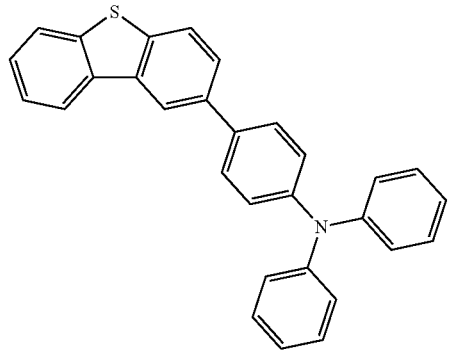

[H1]

-continued

[D1]

[E1]

Example 2

An experiment was performed in the same manner as in Example 1, except that the compound of Formula 1-4 was used as the hole transporting layer instead of the compound of Formula 1-1 synthesized in Synthetic Example 1.

Example 3

An experiment was performed in the same manner as in Example 1, except that the compound of Formula 1-5 was used as the hole transporting layer instead of the compound of Formula 1-1 synthesized in Synthetic Example 1.

Example 4

An experiment was performed in the same manner as in Example 1, except that the compound of Formula 1-6 was used as the hole transporting layer instead of the compound of Formula 1-1 synthesized in Synthetic Example 1.

Example 5

An experiment was performed in the same manner as in Example 1, except that the compound of Formula 1-7 was used as the hole transporting layer instead of the compound of Formula 1-1 synthesized in Synthetic Example 1.

Example 6

An experiment was performed in the same manner as in Example 1, except that the compound of Formula 1-8 was used as the hole transporting layer instead of the compound of Formula 1-1 synthesized in Synthetic Example 1.

Example 7

An experiment was performed in the same manner as in Example 1, except that the compound of Formula 1-9 was used as the hole transporting layer instead of the compound of Formula 1-1 synthesized in Synthetic Example 1.

Example 8

An experiment was performed in the same manner as in Example 1, except that the compound of Formula 1-2 was used as the hole transporting layer instead of the compound of Formula 1-1 synthesized in Synthetic Example 1.

Comparative Example 1

An experiment was performed in the same manner as in Example 1, except that HT1 was used as the hole transporting layer instead of the compound of Formula 1-1 synthesized in Synthetic Example.

Comparative Example 2

An experiment was performed in the same manner as in Example 1, except that NPB was used as the hole transporting layer instead of the compound of Formula 1-1 synthesized in Synthetic Example.

Comparative Example 3

An experiment was performed in the same manner as in Example 1, except that HT2 was used as the hole transporting layer instead of the compound of Formula 1-1 synthesized in Synthetic Example.

Comparative Example 4

An experiment was performed in the same manner as in Example 1, except that HT3 was used as the hole transporting layer instead of the compound of Formula 1-1 synthesized in Synthetic Example.

Each compound was used as a hole transporting layer material as in Examples 1 to 8 and Comparative Examples 1 to 4 to manufacture an organic light emitting device, on which experiment was performed, and the results thereof are shown in Table 1.

TABLE 1

| Experimental Example 50 mA/cm² | HTL material | Voltage (V) | Electric current efficiency (cd/A) |
|---|---|---|---|
| Comparative Example 1 | HT1 | 6.25 | 5.98 |
| Comparative Example 2 | NPB | 6.21 | 5.87 |
| Comparative Example 3 | HT2 | 6.42 | 6.07 |
| Comparative Example 4 | HT3 | 7.11 | 6.53 |
| Example 1 | Formula 1-1 | 6.15 | 7.12 |
| Example 2 | Formula 1-4 | 6.18 | 7.12 |
| Example 3 | Formula 1-5 | 6.11 | 6.99 |
| Example 4 | Formula 1-6 | 6.15 | 7.05 |
| Example 5 | Formula 1-7 | 6.14 | 7.10 |
| Example 6 | Formula 1-8 | 6.15 | 7.12 |
| Example 7 | Formula 1-9 | 6.18 | 7.11 |
| Example 8 | Formula 1-2 | 6.17 | 7.11 |

As can be seen in Table 1, an organic light emitting device manufactured by using the compound of the present invention as a hole transporting layer material shows excellent characteristics in terms of efficiency, driving voltage and stability, when compared to the case of using a material in the related art.

Further, as can be seen in Table 1, an organic light emitting device manufactured by using the compound of the present invention as a hole transporting layer material has an appropriate HOMO level and thus may increase the hole injection efficiency in a light emitting layer, may drive at a low voltage and show excellent characteristics in terms of efficiency compared to when $R_2$ and $R_3$ is an aryl group having less than 10 ring-membered carbon atoms.

In addition, an organic light emitting device manufactured by using the compound of the present invention as a hole transporting layer material has an electron donor effect of S with a linked amine group and may increase the hole injection and transfer efficiency in a light emitting layer, and thus shows excellent characteristics in terms of voltage and efficiency compared to the Comparative Example 4 where the 13th position of dibenzothiophene is substituted with amine.

The invention claimed is:

1. A dibenzothiophene-based compound represented by the following Formula 1:

[Formula 1]

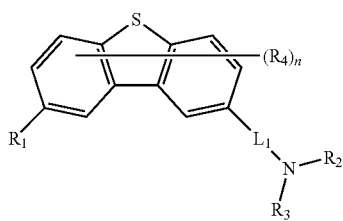

Wherein $L_1$ is an arylene group having 6 to 40 carbon atoms; or a fluorenylene group substituted with an alkyl group, $R_1$ is hydrogen; an alkyl group having 1 to 20 carbon atoms; an alkoxy group having 1 to 20 carbon atoms; or an aryl group having 6 to 12 carbon atoms, which is unsubstituted or substituted with an alkyl group having 1 to 20 carbon atoms or an alkoxy group having 1 to 20 carbon atoms, $R_2$ and $R_3$ are the same as each other, and are each a phenyl group which is substituted with one or more substituents selected from the group consisting of a thiophene group unsubstituted or substituted with a phenyl group and a benzothiophene group, an aryl group having 10 to 16 ring-membered carbon atoms, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group; a carbazole group unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group; a thiophenyl group unsubstituted or unsubstituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group; or a heterocyclic group including one or more of N, S and O atoms and having 5 to 12 ring-membered carbon atoms, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group, $R_4$ is hydrogen; an alkyl group having 1 to 20 carbon atoms; or an alkoxy group having 1 to 20 carbon atoms, and may form an aliphatic, aromatic or hetero condensed ring with an adjacent group, and n means the number of substituents and is an integer of 1 to 6.

2. The dibenzothiophene-based compound of claim 1, wherein $R_1$ is hydrogen or a phenyl group unsubstituted or substituted with an alkyl group having 1 to 20 carbon atoms.

3. The dibenzothiophene-based compound of claim 1, wherein $R_2$ and $R_3$ are the same as each other, and are each an aryl group having 10 to 16 ring-membered carbon atoms, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a fluorenyl group, a carbazole group, a nitrile group, a thiophene group unsubstituted or substituted with a phenyl group, a benzothiophene group and a nitro group.

4. The dibenzothiophene-based compound of claim 1, wherein $R_2$ and $R_3$ are the same as each other, and are each a biphenyl group, which is unsubstituted or substituted with one or more substituents selected from the group consisting of an alkyl group having 1 to 20 carbon atoms, an alkenyl group having 2 to 20 carbon atoms, an alkoxy group having 1 to 20 carbon atoms, a nitrile group and a nitro group; or a phenyl group which is substituted with one or more substituents selected from the group consisting of a thiophene group unsubstituted or substituted with a phenyl group and a benzothiophene group.

5. The dibenzothiophene-based compound of claim 1, wherein $L_1$ is a phenylene group, a biphenylene group or a fluorenylene group unsubstituted or substituted with an alkyl group.

6. The dibenzothiophene-based compound of claim 1, wherein $L_1$ is a phenylene group, a biphenylene group or a fluorenylene group substituted with an alkyl group,
   $R_1$ is hydrogen, or a phenyl group unsubstituted or substituted with an alkyl group having 1 to 20 carbon atoms, and
   $R_2$ and $R_3$ are the same as each other, and are each a biphenyl group, a phenyl group substituted with a thiophene group unsubstituted or substituted with a phenyl group, or a phenyl group substituted with benzothiophene.

7. The dibenzothiophene-based compound of claim 1, wherein Formula 1 is any one of Formulas 1-1 to 1-9

[Formula 1-1]

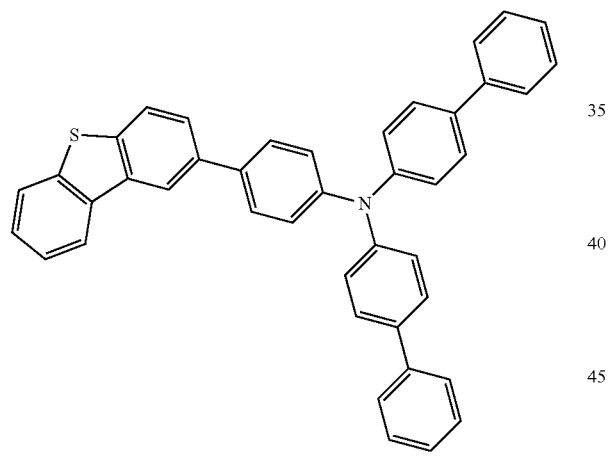

[Formula 1-2]

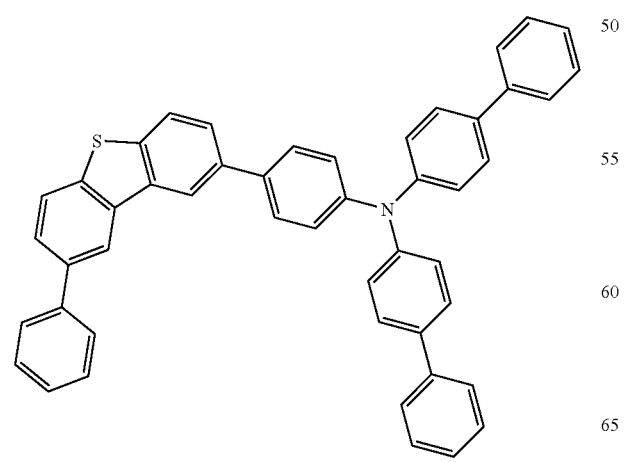

[Formula 1-3]

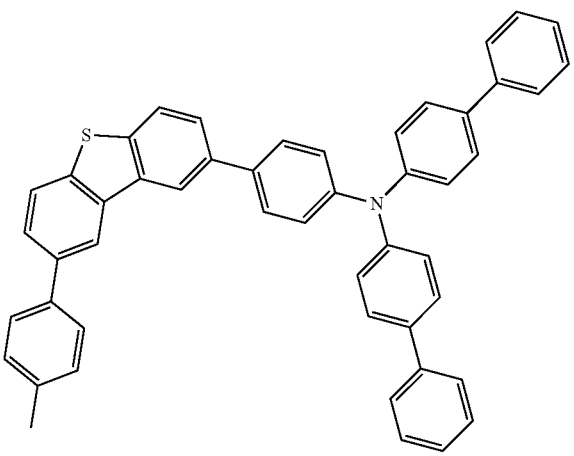

[Formula 1-4]

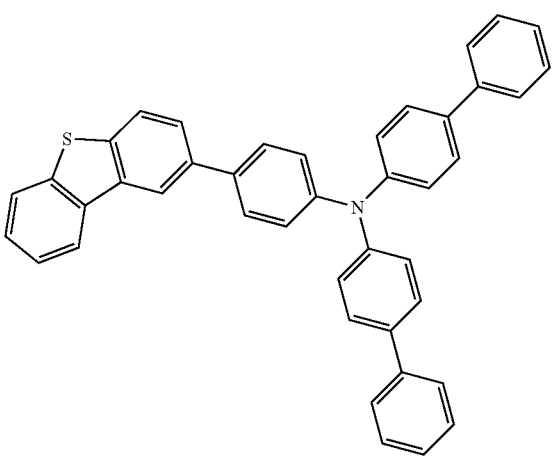

[Formula 1-5]

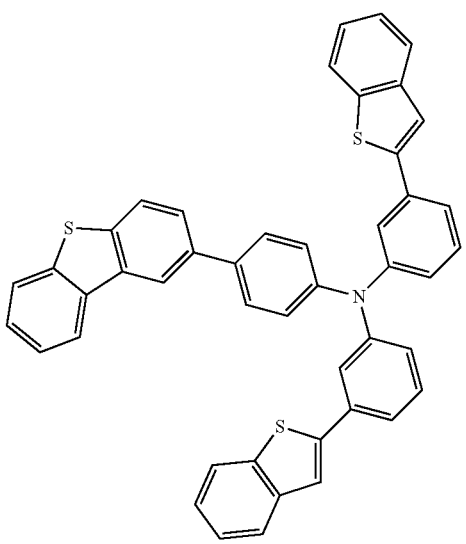

[Formula 1-6]

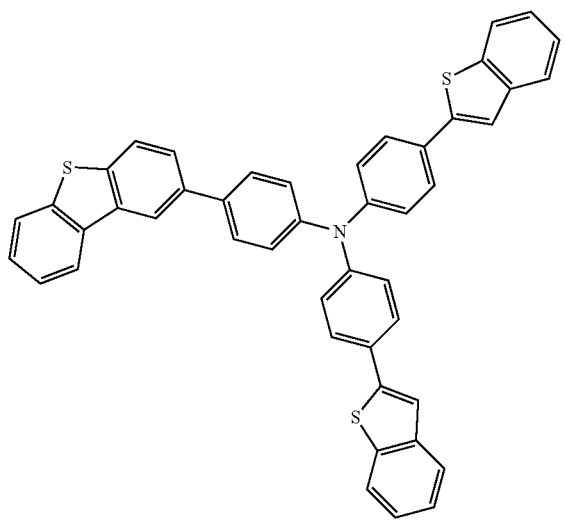

[Formula 1-7]

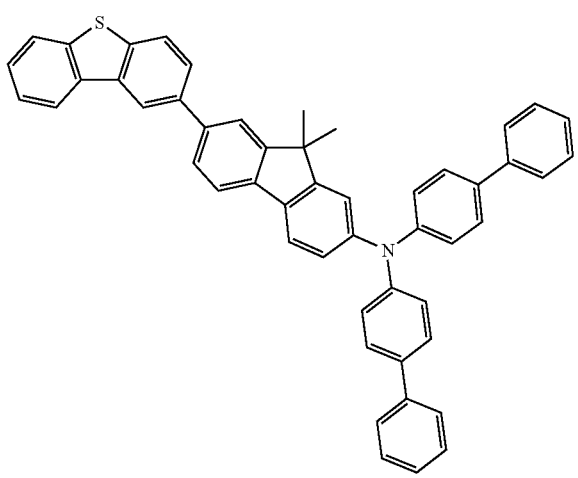

[Formula 1-8]

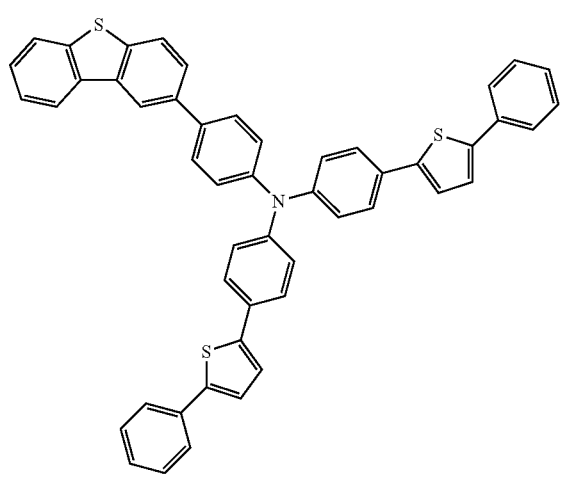

[Formula 1-9]

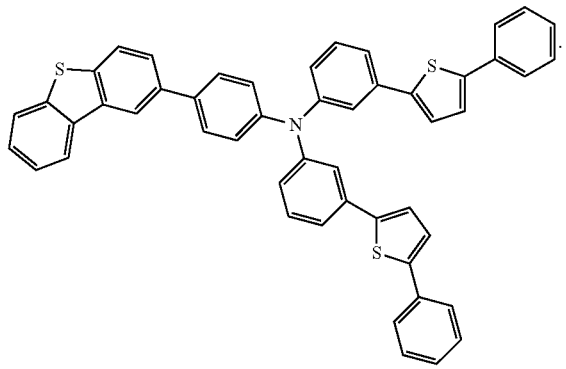

8. An organic light emitting device comprising an organic material layer composed of one more layers comprising a first electrode, a second electrode and a light emitting layer disposed between the first electrode and the second electrode, wherein one or more layers of the organic material layer comprise the dibenzothiophene-based compound of claim 1.

9. The organic light emitting device of claim 8, wherein the organic material layer comprises a hole transporting layer and the hole transporting layer comprises the dibenzothiophene-based compound.

10. The organic light emitting device of claim 8, wherein the organic material layer comprises a two-layered hole transporting layer and at least one layer of the hole transporting layer comprises the dibenzothiophene-based compound.

11. The organic light emitting device of claim 8, wherein the organic material layer comprises a first hole transporting layer and a second hole transporting layer,
the first hole transporting layer comprises the dibenzothiophene-based compound, and
the second hole transporting layer comprises an aromatic amine compound.

12. The organic light emitting device of claim 11, wherein the first hole transporting layer is interposed between a light emitting layer and the second hole transporting layer.

13. The organic light emitting device of claim 11, wherein the first hole transporting layer is in contact with the light emitting layer.

14. The organic light emitting device of claim 8, wherein the organic material layer comprises a hole injection layer and the hole injection layer comprises the dibenzothiophene-based compound.

15. The organic light emitting device of claim 8, wherein the organic material layer comprises a layer that simultaneously injects and transports holes and the layer comprises the dibenzothiophene-based compound.

16. The organic light emitting device of claim 8, wherein the organic material layer comprises an electron injection and electron transporting layer and the electron injection or electron transporting layer comprises the dibenzothiophene-based compound.

17. The organic light emitting device of claim 8, wherein the organic material layer comprises a light emitting layer and the light emitting layer comprises the dibenzothiophene-based compound.

* * * * *